Dec. 11, 1951 P. ECKE Plant Pat. 1,052
POINSETTIA PLANT
Filed July 6, 1950
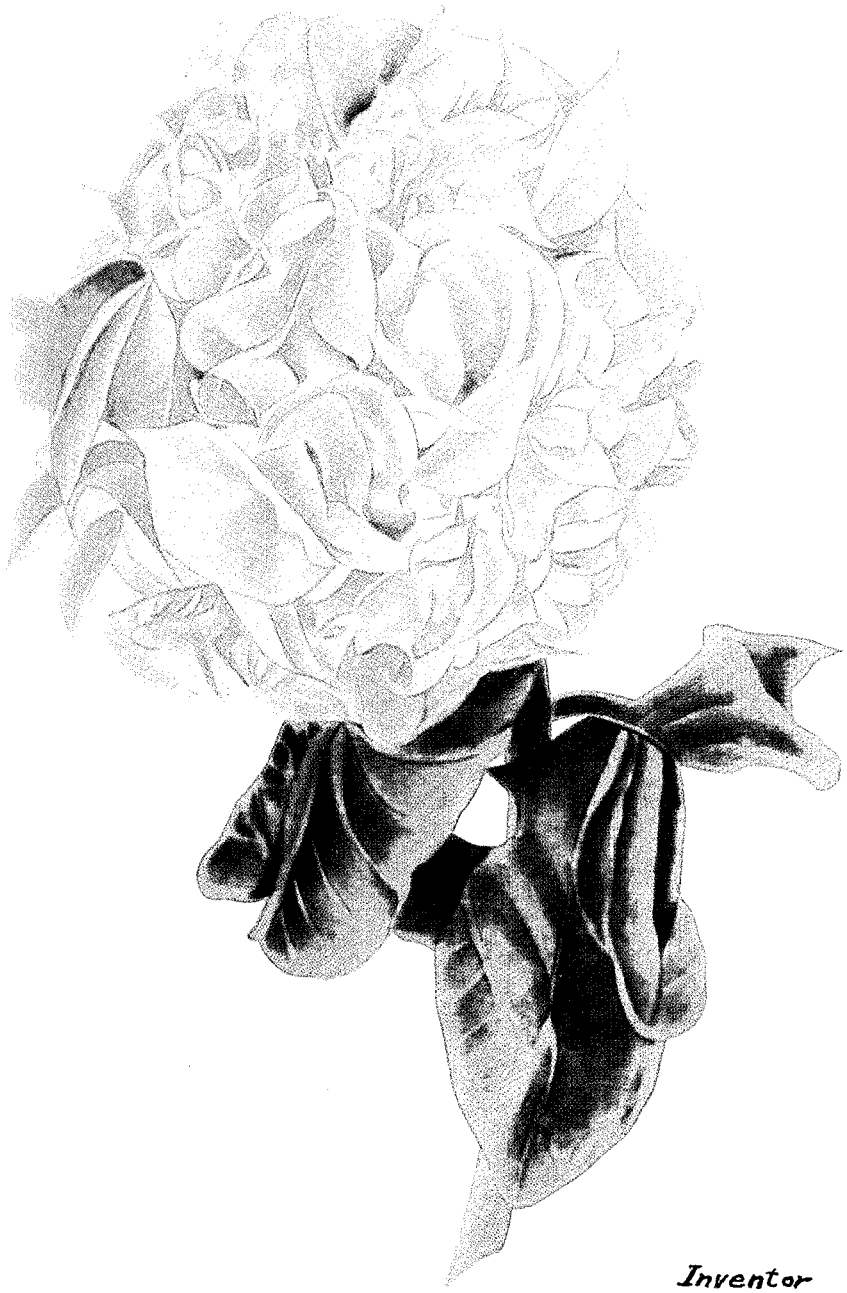
Inventor
Paul Ecke
By Mm. J. Graham
Attorney Patented Dec. 11, 1951

Plant Pat. 1,052

UNITED STATES PATENT OFFICE 1,052

POINSETTIA PLANT

Paul Ecke, Encinitas, Calif.

Application July 6, 1950, Serial No. 172,291

1 Claim. (Cl. 47—60)

The present invention and discovery relates to a new and distinct variety of poinsettia plant (*Euphorbia pulcherrima*) originating as a sport.

Broadly, this new variety of poinsettia plant is distinguishable from the parent plant, as well as from other known varieties, mainly by the color, shape and characteristic of bracts to form a head, and the curling of the midrib of the foliage leaves.

The accompanying illustration forming a part of this specification, graphically shows in color the subject in its full maturity, the illustration being a face view of the subject shown at its optimum condition with its distinctive characteristics.

The colors mentioned herein correspond approximately to those shown in "Horticultural Color Chart," issued by the British Color Council in collaboration with the Royal Horticultural Society, and identified by the color name and plate of said color standard by recapitulation in tabular form herein.

The following is a detailed description of this new variety:

*Parentage*

This new variety is a sport of a poinsettia plant of a variety generally known as a double bract type, the parent of the new variety being referred to as a Henrietta Ecke variety, not patented, and which is described at page 508 in "Florist Crop Production and Marketing," by Kenneth Post. This new variety was originated and discovered by me in my glassed house at Encinitas, California, and has been asexually reproduced by me at Encinitas, California, from cuttings. The new variety has remained true to type and the herein described characteristics through propagation of several thousand plants over a period of more than three years and its qualities and characteristics have been demonstrated to have become permanently fixed.

*Structure*

Peduncles which branch from the main trunk are scheeles green, and are stiff, strong and comparatively large in section, their average length being four feet, with several small knob-like spurs growing expansively apart at the upper end, from which grow the bracts, and a malformed inflorescence, as hereinafter described.

*Petioles*

Extending outwardly from around each of the peduncles is a plurality of foliage leaves, the petioles of which are attached to and arranged helically around the peduncles. The petioles are of spinach green color, and are arcuate and uncommonly thick.

*Foliage leaves*

The foliage leaves are of spinach green color; in shape they are generally irregularly ovate in a flat plane, lacking the conspicuous pinnatilobate character of the oak leaf type. Venation is prominent and branches from the midrib in substantial parallelism. At early stages of maturity of the foliage leaves the midrib is in substantially straight alignment, but as the bracts develop to an optimum of color, the midrib of the foliage leaves develops a curvature in direction toward the under or reverse face of the leaf, which increases as the bracts mature, and finally, when the bracts begin to drop from the headed cluster, the midrib will have become substantially spirally curved so that the lobes of the blade at opposite sides of the midrib are drawn upwardly relative to the obverse face, resembling a pair of butter-fly wings. Foliage leaves in various stages are illustrated in the drawing: in the center is a leaf in substantially ovate form; the leaf at the left has its midrib partly arcuate at its apex, while the leaf at the right has an increased curvature to its midrib. Another characteristic of the foliage leaves is the tendency to roll at the perimeter as the midrib increases in curvature, sometimes rolling toward the front or upper face of the leaf and sometimes towards the under or reverse face of the leaf as illustrated in the respective leaves at the right and left in the drawing.

*Bracts*

The bracts are very numerous and grow from the knob-like spurs or pedicels at the head end of the peduncles. The bracts form a closely or densely compacted head, and individually the bracts are exceedingly geometrically tortuous and sinuously overlapping or crinkly, the perimeter edge portion being ruffled. The bracts at the central portion of the clustered head are less tortuous and ruffled than the bracts adjacent the circumferential portion of the head. The petioles of the bracts are relatively short which maintain the head in a closely clustered ball at optimum of development. In color the bracts are blood-red.

*Inflorescence*

In this new variety there is no substantial or apparent normally developed inflorescence during the period of development and growth of the bracts. After the bracts have developed to optimum in a head and are in a state of declination, each of the nob-like pedicellate spurs develops at its terminal end a malformation of a perianth, but the usual cyathium, stamens, pistil, ovules, and other attributes of inflorescence common to other varieties of poinsettia plants do not develop.

*Habits of growth*

This new variety is vigorous, but slow in growth, easily cultivated if properly handled, and persistent and perennial in growth. Foliage and bracts occur annually maturing in Southern California from November to December, the optimum elsewhere being modified by climate and growing conditions. The entire plant seems to be immune or highly resistant to insects, disease and all other obnoxious and detrimental interferences with normal growth. The total height of the plant at maturity, including main trunk and peduncles, is approximately 6 to 8 feet, and the lateral dimension is approximately 4 to 5 feet.

*Variations*

Different plants of this new variety have unusual similarity of adherence to characteristics and type. However, in comparison with the same grown in various localities, in different soil and at various times of the year in different temperatures or in different greenhouses or in the open, and even by different persons there may be slight variations of minor details.

*Propagation*

Propagation is by cuttings planted at any time from May until September, and the plant will mature to optimum from November to December, retaining bracts and foliage for substantially two months, after which the plant will remain dormant for about three months.

*Color tabulation*

The color designations according to the color plates of said "Horticultural Color Chart" are recapitulated in tabular form as follows:

| Element | Color | Sheet | Plate |
|---|---|---|---|
| Peduncle | Scheeles Green | 175 | 860 |
| Petioles | Spinach Green | 187 | o960/1 |
| Foliage Leaves | do | 187 | 0960/1 |
| Bracts | Blood-Red | 166 | 820/2 |

Having described and illustrated this new variety of poinsettia plant, I claim:

A new and distinct variety of poinsettia plant substantially as illustrated and described, characterized by a profusion of blood-red geometrically tortuous bracts sinuously overlapping in dense, closely compacted head, and foliage leaves which, at optimum of development of the bracts, have their midrib arcuately curved towards the underface of the foliage leaves.

PAUL ECKE.

No references cited.